United States Patent

Karbach et al.

[11] Patent Number: 4,822,908
[45] Date of Patent: Apr. 18, 1989

[54] SUBSTITUTED ACRYLATES AND FUNGICIDES CONTAINING SAME

[75] Inventors: Stefan Karbach, Ludwigshafen; Ulrich Schirmer; Costin Rentzea, both of Heidelberg; Ernst-Heinrich Pommer, Limburgerhof; Eberhard Ammermann, Ludwigshafen; Wolfgang Steglich, Bonn-Roettgen; Barbara A. M. Schwalge, Lohmar; Timm Anke, Kaiserslautern, all of Fed. Rep. of Germany

[73] Assignee: BASF Aktiengesellschaft, Lugwigshafen, Fed. Rep. of Germany

[21] Appl. No.: 64,126

[22] Filed: Jun. 19, 1987

[30] Foreign Application Priority Data

Jun. 21, 1986 [DE] Fed. Rep. of Germany ....... 3620860

[51] Int. Cl.⁴ .............................................. C07C 69/76
[52] U.S. Cl. ........................................ 560/60; 560/10; 560/23; 558/389; 558/398
[58] Field of Search .............................. 560/60, 10, 23; 558/389, 398; 514/132

[56] References Cited
FOREIGN PATENT DOCUMENTS
178826 4/1986 European Pat. Off. .

Primary Examiner—Paul J. Killos
Attorney, Agent, or Firm—Oblon, Fisher, Spivak, McClelland & Maier

[57] ABSTRACT

Substituted acrylates of the general formula

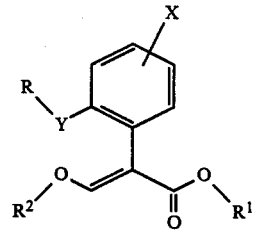

where $R^1$ and $R_2$ are alkyl, alkenyl or alkynyl, X is hydrogen, halogen, alkyl, alkoxy, tirfluoromethyl, cyano or nitro, Y is ethylene, ethenylene, methyleneoxy, oxymethylene, thiomethylene, methylenethio or oxygen, R is hydrogen, substituted or unsubstituted alkyl, cycloalkyl, alkenyl, cycloalkenyl, alkynyl or cycloalkynyl, and fungicides containing these compounds.

7 Claims, No Drawings

SUBSTITUTED ACRYLATES AND FUNGICIDES CONTAINING SAME

The present invention relates to novel substituted acrylic acid derivatives and fungicides which contain these compounds.

It is known to use N-tridecyl-2,6-dimethylmorpholine or salts thereof, for example the acetate, as fungicides (DE Nos. 1,164,152, 1,173,722). However, their activity is inadequate in some cases. It is further known to use acrylic acid derivatives, for example methyl alpha(2-benzyloxyphenyl)-beta-methoxy acrylate, as a fungicide (EP No. 178,826). Its fungicidal activity is unsatisfactory.

We have now found that novel acrylic acid derivatives of the formula $$\text{[structure]}$$

where
  $R^1$ and $R^2$ are independently of each other $C_1$–$C_8$-alkyl, $C_2$–$C_8$-alkenyl or $C_3$–$C_8$-alkynyl,
  X is hydrogen, halogen, $C_1$–$C_4$-alkyl, $C_1$–$C_4$-alkoxy, trifluoromethyl, cyano or nitro,
  Y is ethylene, ethenylene, methyleneoxy, oxymethylene, thiomethylene, methylenethio or oxygen,
  R is hydrogen or unsubstituted or $C_1$–$C_4$-alkoxy-, halogen-, cyano- or $COOR^3$- substituted $C_1$–$C_{20}$-alkyl, $C_3$–$C_8$-cycloalkyl, $C_2$–$C_{20}$-alkenyl, $C_6$–$C_8$-cycloalkenyl, $C_3$–$C_{10}$-alkynyl or $C_8$-cycloalkynyl and
  $R^3$ has the same meanings as $R^1$ and is identical to or different from $R^1$,
have an excellent fungicidal action.

The radicals featured in the general formula can for example have the following meanings:
  $R^1$ and $R^2$ can each be $C_1$–$C_8$-alkyl (eg. methyl, ethyl, isopropyl, n-propyl, n-butyl, s-butyl, t-butyl, i-butyl, s-pentyl, n-hexyl, 2-ethyl-n-hexyl, n-octyl), $C_2$–$C_8$-alkenyl (eg. vinyl, allyl, 1-methyl-2-propenyl, 3-methylbutenyl, 3-methyl-2-butenyl, 2-methyl-3-butenyl, 4-octenyl), $C_3$–$C_8$-alkynyl (eg. propargyl, 3-butynyl, 2-methylbutyn-2-yl, 4-octynyl),
  X can be hydrogen, halogen (eg. fluorine, chlorine, bromine), $C_1$–$C_4$-alkoxy (eg. methoxy, n-butoxy), $C_1$–$C_4$-alkyl (methyl, ethyl, propyl, butyl), trifluoromethyl, cyano or $NO_2$,
  Y can be ethylene (—$CH_2$—$CH_2$—), ethenylene (—CH=CH—), methyleneoxy (—$CH_2$—O), oxymethylene (—O—$CH_2$—), thiomethylene (—S—$CH_2$—), methylenethio (—$CH_2$—S—) or —O—,
  R can be hydrogen or unsubstituted or $C_1$–$C_4$-alkoxy-, halogen-, cyano- or $COOR^1$- substituted $C_1$–$C_{18}$-alkyl (eg. methyl, ethyl, n-pentyl, n-decyl, n-pentadecyl, n-octadecyl, n-eicosanyl, methoxyethyl, butoxyethyl, methoxycarbonylethyl), $C_3$–$C_8$-cycloalkyl (eg. cyclopropyl, gem.-dichlorocyclopropyl, cyclohexyl, cyclooctyl), $C_2$–$C_{20}$-alkenyl (eg. allyl, 2-butenyl, 2,6-dimethyl-2,6-octadienyl), $C_6$–$C_8$-cycloalkenyl (eg. cyclohexenyl, cyclooctadienyl), $C_3$–$C_{10}$-alkynyl (eg. propargyl, 2-butynyl, decyn-10-yl) or $C_8$-cycloalkynyl (eg. cyclooctynyl).

The novel compounds may contain double bonds and chiral centers. The present invention embraces not only the double bond isomers but also any enantiomers and diastereomer isomers. With regard to their use as fungicides, it is possible to use not only the individual isomers but also mixtures thereof produced in the course of preparation.

The novel compounds can be prepared for example by the following method:

A 2-methylphenyl acetate of the general formula $$\text{[structure: } CH_2-COOR^1\text{ on phenyl with } H_3C \text{ and } X\text{]}$$

is made to react by the method of Wislicenus (Liebigs Annalen 424 (1921), 215 and 413 (1917), 206) with methyl formate and sodium hydride in an inert solvent. The resulting compound of the general formula $$\text{[structure with } R^1OOC, OH, H_3C, X\text{]}$$

is reacted with an alkylating agent in the presence of a base in a solvent (for example acetone) to give an α-(2-methylphenyl)-β-alkoxyacrylic acid ester $$\text{[structure with } R^1OOC, OR^2, H_3C, X\text{]}$$

where $R^1$, $R^2$ and X have the abovementioned meanings.

The bromination of this compound with N-bromosuccinimide (Horner, Winkelmann, Angew. Chemie 71 (1959), 349) leads to an α-(2-bromomethylphenyl)-β-alkoxyacrylic acid ester, which can be made to react with a trialkyl phosphite to give a phosphonate of the general formula:

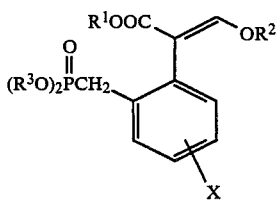

where $R^1$, $R^2$ and X have the abovementioned meanings and $R^3$ is $C_1$-$C_8$-alkyl (Houben-Weyl, Methoden der organischen Chemie 12/1 (1963), 433).

The abovementioned phosphonate is reacted with a substituted or unsubstituted alkyl-, alkenyl- or alkynylaldehyde:

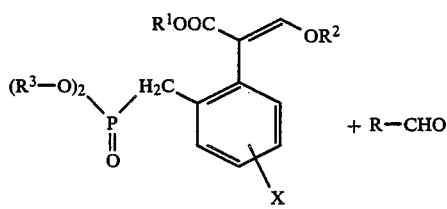

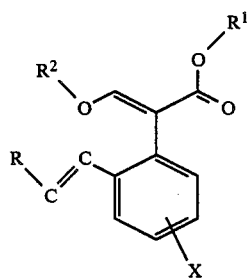

The unsaturated derivative thus obtained can be selectively reduced either catalytically with hydrogen (cf. Houben-Weyl, Methoden der organischen Chemie V/2b (1981), 264-7) or with diimine (cf. Houben-Weyl, Methoden der organischen Chemie IV/1c, 580 and E. E. van Tamelen, R. S. Dewey, M. F. Lease, W. H. Pirkle, JACS 83 (1961), 4302) to give a novel alkoxyacrylic acid derivative:

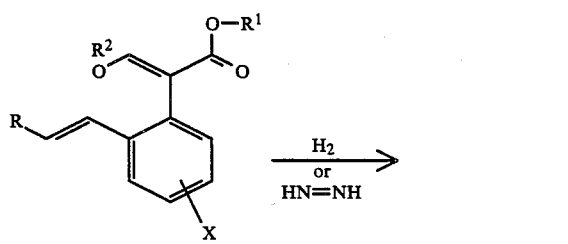

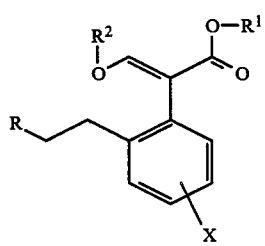

The bromomethylphenylalkoxyacrylic acid ester obtained as an intermediate can be reacted with an alcoholate or thiolate in a suitable solvent (eg. tetrahydrofuran, dimethylformamide, dimethyl sulfoxide, a thiol, diethyl ether, toluene, benzene, xylene, methyl t-butyl ether) to give the corresponding alkoxy or alkylthio derivative

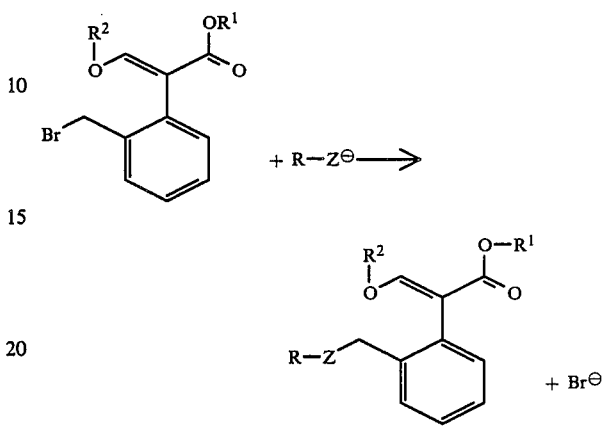

where Z is O or SH.

The novel compounds can also be prepared for example as follows:

A 2-hydroxyphenyl acetate alkylated with R can be formylated at the methylene group of the acetate radical as described above and then alkylated.

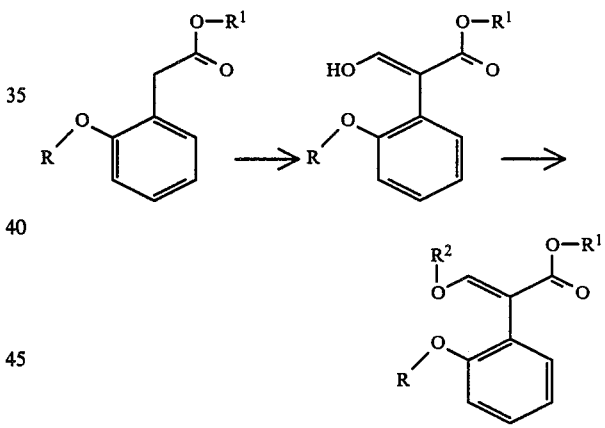

The methods which follow illustrate the preparation of the starting compounds:

METHOD A

Methyl α-(2-methylphenyl)-β-methoxyacrylate 16.5 g of methyl 2-methyl phenyl acetate are dissolved in 10 ml of methyl formate, and the solution is slowly added dropwise to a suspension of 3 g of sodium hydride in 150 ml of absolute ether. The mixture is refluxed for 4 h and then acidified with dilute HCl, and the organic phase is separated off, washed with water, dried over $MgSO_4$ and concentrated. This gives 13.8 g of a pale yellow oil (methyl α-formyl-(2-methylphenyl)acetate), which is refluxed for 1 h together with 5.8 ml of dimethyl sulfate, 10.9 g of potassium carbonate and 70 ml of acetone. Filtration and concentrating is followed by taking up in ether and washing with dilute aqueous ammonia and repeatedly with water. Removal of the ether leaves 11.3 g of crude methyl α-(2-methylphenyl)-β-methoxyacrylate (bp 102°–108° C./0.05 mm Hg).

NMR in CDCl$_3$: 7.63, s 1H; 7.16–7.36, bs 4H; 3.64, s 3H; 3.73, s 3H; 2.16, s 3H.

METHOD B

Methyl α-(2-bromomethylphenyl)-β-methoxyacrylate 20.6 g of the methyl α-(2-methylphenyl)-β-methoxyacrylate obtained by Method A, 17.65 g of N-bromosuccinimide, 0.2 g of azodiisobutyronitrile and 150 ml of CCl$_4$ are slowly heated to 90° C. This temperature is maintained until all the succinimide is floating on the solvent. Filtration is followed by concentrating, the remaining oil is dissolved in about 5 ml of acetone, and n-hexane is added to bring about crystallization. This gives 27.5 g of colorless crystals of mp 86°–87° C.

METHOD C

Dimethyl 2-(β-methoxy-α-methoxycarbonylvinyl)benzylphosphate 28.5 g of methyl α-(2-bromomethylphenyl)-β-methoxyacrylate are refluxed for one hour with 11.8 ml of trimethyl phosphite and 6.5 ml of toluene. The reaction mixture is carefully concentrated under reduced pressure, and the remaining oil is dissolved in 5 ml of ether and then crystallized with n-hexane. This gives 27.3 g of colorless crystals of mp 94° C.

METHOD D

Methyl 2-n-butoxyphenylacetate 16.6 g of methyl 2-hydroxyphenyl acetate are dissolved in 100 ml of methanol. 15 g of potassium carbonate and 18 g of n-butyl bromide are added. After 24 hours of refluxing followed by filtration, the solution is concentrated under reduced pressure. The oil obtained is taken up in diethyl ether and washed with NaHCO$_3$ and H$_2$O. Drying over sodium sulfate and removal of the solvent leaves 14.5 g (65%) of a yellow oil which can be purified by distillation.

NMR in CDCl$_3$: m 7.15 2H, m 6.85 2H, t 3.95 —CH$_2$—, s 3.65 0—CH$_3$, s 3.62 —CH$_2$—, m 1.75 —CH$_2$—, m 1.48 —CH$_2$—, t 0.95 —CH$_3$

METHOD E

Methyl α-formyl-(2-butoxyphenyl)acetate 11.1 g of the product obtained by Method D are dissolved in 50 ml of methyl formate, and the solution is slowly added at 0° C. to 3.5 g of sodium methylate. The mixture is warmed to room temperature, and the bulk of the methyl formate is removed under reduced pressure. The remainder is poured onto cold 2N NaOH, and the mixture is extracted with 30 ml of methyl t-butyl ether. The aqueous phase is acidified, and the methyl α-formyl(2-butoxyphenyl)acetate is extracted with dichloromethane. Drying the organic phase over Na$_2$SO$_4$ gives 10.2 g (82%) of pure product.

EXAMPLE 1

Methyl α-(2-(2,6-dimethyloctanyloxy)phenyl)-β-methoxyacrylate (Compound 2)

3.2 g of methyl α-(2-(2,6-dimethylocta-2,6-dienyloxy)phenyl)-β-methoxyacrylate are dissolved in 70 ml of methanol, and 0.2 g of palladium on active carbon is added. At room temperature, hydrogen is passed with stirring through the suspension until no further gas is absorbed. The solution is separated from the catalyst and evaporated. This give 3.1 g of an oil.

EXAMPLE 2

Methyl α-(2-n-butoxyphenyl)-3-methoxyacrylate (Compound 7)

10 g of methyl α formyl-(2-butoxyphenyl)acetate are dissolved in 100 ml of acetone. 15 g of potassium carbonate are added, followed gradually with stirring by an equimolar amount of dimethyl sulfate. After 12 hours of refluxing, 50 ml of H$_2$O are added, followed carefully by 30 ml of concentrated NH$_3$ solution. After 2 hours of stirring, about 100 ml of solvent are drawn off, poured onto ice and extracted with dichloromethane. Drying of the organic phase leaves 8.7 g of oil.

EXAMPLE 3

1.44 g of NaH (80% pure) are presented under nitrogen in 20 ml tetrahydrofuran (THF). 15 g of phosphonate from Method C and 5.4 g of cyclohexylaldehyde are dissolved in 100 ml of THF, and the solution is slowly added dropwise and with stirring to the NaH. The reaction mixture is stirred for 10 hours, and 200 ml of H$_2$O are then added dropwise. After extraction with dichloromethane, the organic phase is dried over Na$_2$SO$_4$ and evaporated under reduced pressure. The residue is dissolved in toluene and filtered through silica gel. 9.3 g of a resin (Compound 10) are obtained.

EXAMPLE 4

Methyl α-(2-butoxymethylphenyl)-β-methoxyacrylate (Compound 32)

7.4 g of n-butanol are dissolved in 50 ml of dimethylformamide, and 2.4 g of sodium hydride are added. The solution is slightly heated until everything has reacted. This solution is gradually added dropwise at −20° C. to 28.4 g of methyl α-(2-bromomethylphenyl)-β-methoxyacrylate in 150 ml of THF. Once the bromomethyl compound is no longer detectable by thin layer chromatography, 100 g of ice and 100 ml of saturated NaCl solution are added. Extraction with methylene chloride gives 23 g of an oil which is chromatographed. 10 g of a resin are obtained after elution with ethyl acetate/hexane.

EXAMPLE 5

Methyl α-2-hydroxyphenyl-β-methoxyacrylate (Compound 76)

A spatula tip of palladium on active carbon is added to 40 g of methyl α-(2-benzyloxyphenyl)-β-methoxyacrylate in 400 ml of THF, the mixture is heated to 50° C. Hydrogen is then slowly passed through under atmospheric pressure with stirring until the starting material is no longer detectable by thin layer chromatography. The solution is filtered through silica gel, washed with 200 ml of THF and evaporated under reduced pressure. Recrystallization of the residue from methyl t-butyl ether and petroleum ether gives 27.6 g (99%) of methyl α-2-hydroxyphenyl-β-methoxy acrylate of mp 129° C.

The same method can be used to prepare the following compounds:

| No. | R¹ | R² | (R—Y—aromatic) | X | R | NMR (CDCl$_3$; ppm) |
|---|---|---|---|---|---|---|
| 1 | CH$_3$ | CH$_3$ | —CH$_2$—O— | H | 2,6-dimethyl-2,6-heptadienyl | s 7.43 1H; m 7.6–6.8 4H; t 5.4 1H; 2 506; d 4.5; 2 3.73; s 3.6; m 2.3; m 1.7; m 1.6 |
| 2 | CH$_3$ | CH$_3$ | —CH$_2$—O— | H | 2,6-dimethylheptyl | 2 7.42 1H; m 7.6–6.8 4H; m 3.9 2H; s 3.8–5H; s 3.63 3H; m 0.7–2.25 |
| 3 | CH$_3$ | CH$_3$ | —CH$_2$—O— | H | 2,6,10-trimethyl-2,6,10-undecyltrienyl | m 7.5–6.7 5H; s 5.3 1H; s 5.0 2H; s 3.8 3H; s 3.73 2H; 2 3.70 3H; m 1.7–2.1 |
| 4 | CH$_3$ | CH$_3$ | —CH$_2$—O— | H | 2,6,10,14-tetramethyl-2,6,10,14-pentadecatetraenyl | m 7.5–6.7 5H; t 5.4 1H; s 5.01 1H; s 3.8 3H; s 3.65 3H; s 3.6 5H; m 1.5–2.0 |
| 5 | CH$_3$ | CH$_3$ | —CH$_2$—O— | H | n-C$_{20}$H$_{41}$ | |
| 6 | CH$_3$ | CH$_3$ | —CH$_2$—O— | H | n-C$_{10}$H$_{21}$ | |
| 7 | CH$_3$ | CH$_3$ | —CH$_2$—O— | H | n-C$_3$H$_7$ | s 7.45; m 7.3–6.8 4H; t 3.95 2H; s 3.3 3H; s 3.15 3H; m 1.8–1.6 2H; m 1.55–1.35 2H; t 0.95 3H |
| 8 | CH$_3$ | CH$_3$ | —CH$_2$—O— | H | CH$_3$ | |
| 9 | CH$_3$ | CH$_3$ | —CH$_2$—O— | H | H | s 7.49 1H; m 7.44–6.78 4H; s 3.78 6H; s 3.69 3H |
| 10 | CH$_3$ | CH$_3$ | —CH=CH— | H | cyclo C$_6$H$_{11}$ | s 7.58 1H; m 7.51 1H; m 7.18 3H; d 6.25 1H; m 6.05 1H; s 3.78 3H; s 3.65 1H, m 0.8–2.2 10H |
| 11 | CH$_3$ | CH$_3$ | —CH=CH— | H | cyclo C$_5$H$_9$ | |
| 12 | CH$_3$ | CH$_3$ | —CH=CH— | H | cyclo C$_7$H$_{13}$ | |
| 13 | CH$_3$ | CH$_3$ | —CH=CH— | H | cyclo C$_8$H$_{15}$ | |
| 14 | CH$_3$ | CH$_3$ | —CH=CH— | H | 2,6-dimethyl-2,6-heptadienyl-7- | m 7.60 1H; s 7.55 1H; m 7.3–6.85 4H; m 6.35 1H; m 5.95 1H; m 5.1 1H; s 3.78 3H; s 3.66 1H; m 2.35–2.0 4H; d 1.85 3H; 2 1.7 3H; s 1.6 3H |
| 15 | CH$_3$ | CH$_3$ | —CH=CH— | H | CH$_3$ | |
| 16 | CH$_3$ | CH$_3$ | —CH=CH— | H | C$_2$H$_5$ | |
| 17 | CH$_3$ | CH$_3$ | —CH=CH— | H | C$_3$H$_7$ | |
| 18 | CH$_3$ | CH$_3$ | —CH=CH— | H | iso C$_3$H$_6$ | |
| 19 | CH$_3$ | CH$_3$ | —CH=CH— | H | C$_4$H$_9$ | |
| 20 | CH$_3$ | CH$_3$ | —CH=CH— | H | tert. C$_4$H$_9$ | |
| 21 | CH$_3$ | CH$_3$ | —CH=CH— | H | n-C$_{10}$H$_{21}$ | |
| 22 | CH$_3$ | CH$_3$ | —CH=CH— | H | n-C$_{20}$H$_{41}$ | |
| 23 | CH$_3$ | CH$_3$ | —CH=CH— | H | allyl | |
| 24 | CH$_3$ | CH$_3$ | —CH=CH— | H | 1-methyl-2-propenyl | |
| 25 | CH$_3$ | CH$_3$ | —CH=CH— | H | 1-methyl-2-propinyl | |
| 26 | CH$_3$ | CH$_3$ | —CH=CH— | H | 2-propinyl | |
| 27 | CH$_3$ | CH$_3$ | —CH$_2$—CH$_2$— | H | cyclohexyl | s 7.55 1H; m 7.3–6.9 4H; s 3.8 3H; s 3.65 3H; m 2.42 2H; m 1.8–0.8 |
| 28 | CH$_3$ | CH$_3$ | —CH$_2$—CH$_2$— | H | n-butyl | |
| 29 | CH$_3$ | CH$_3$ | —CH$_2$—CH$_2$— | H | n-dodecyl | |
| 30 | CH$_3$ | CH$_3$ | —O—CH$_2$— | H | methyl | |
| 31 | CH$_3$ | CH$_3$ | —O—CH$_2$— | H | ethyl | |
| 32 | CH$_3$ | CH$_3$ | —O—CH$_2$— | H | n-butyl | |
| 33 | CH$_3$ | CH$_3$ | —O—CH$_2$— | H | n-decyl | |
| 34 | CH$_3$ | CH$_3$ | —O—CH$_2$— | H | 1-methyl-2-propenyl | |
| 35 | CH$_3$ | CH$_3$ | —O—CH$_2$— | H | 2-propinyl | |
| 36 | CH$_3$ | CH$_3$ | —O—CH$_2$— | H | 2-propenyl | |
| 37 | CH$_3$ | CH$_3$ | —O—CH$_2$— | H | cyclohexyl | |
| 38 | CH$_3$ | CH$_3$ | —O—CH$_2$— | H | cycloheptyl | |
| 39 | CH$_3$ | CH$_3$ | —O—CH$_2$— | H | cyclopentyl | |
| 40 | CH$_3$ | CH$_3$ | —O—CH$_2$— | H | cyclohexen | |
| 41 | CH$_3$ | CH$_3$ | —O—CH$_2$— | H | methoxyethyl | |
| 42 | CH$_3$ | CH$_3$ | —O—CH$_2$— | H | butoxyethyl | |
| 43 | CH$_3$ | CH$_3$ | —O—CH$_2$— | H | methoxycarbonylethyl | |
| 44 | CH$_3$ | CH$_3$ | —O—CH$_2$— | H | 4-chlorobutyl | |
| 45 | CH$_3$ | CH$_3$ | —CH$_2$—O— | H | 4-chloropropyl | |
| 46 | CH$_3$ | CH$_3$ | —CH$_2$—O— | H | 4-bromobutyl | |
| 47 | CH$_3$ | allyl | —CH=CH— | H | cyclo C$_6$H$_{11}$ | |
| 48 | CH$_3$ | allyl | —CH=CH— | H | CH$_3$ | |
| 49 | CH$_3$ | allyl | —CH=CH— | H | n-C$_4$H$_9$ | |
| 50 | CH$_3$ | propargyl | —CH=CH— | H | cyclo C$_4$H$_{11}$ | |
| 51 | CH$_3$ | propargyl | —CH=CH— | H | CH$_3$ | |
| 52 | CH$_3$ | propargyl | —CH=CH— | H | n-C$_4$H$_9$ | |
| 53 | CH$_3$ | propargyl | —CH=CH— | H | 1-methyl-2-propenyl | |
| 54 | CH$_3$ | propargyl | —CH$_2$—O— | H | n-propyl | |
| 55 | CH$_3$ | propargyl | —CH$_2$—O— | H | CH$_3$ | |
| 56 | CH$_3$ | propargyl | —CH$_2$—O— | H | 1-methyl-2-propenyl | |
| 57 | CH$_3$ | propargyl | —CH$_2$—O— | H | cyclohexyl | |
| 58 | CH$_3$ | allyl | —CH$_2$—O— | H | cyclohexyl | |
| 59 | CH$_3$ | allyl | —CH$_2$—O— | H | 3-butenyl | |
| 60 | CH$_3$ | allyl | —CH$_2$—O— | H | CH$_3$ | |
| 61 | CH$_3$ | allyl | —CH$_2$—O— | H | n-propyl | |
| 62 | CH$_3$ | allyl | —CH=CH— | 4F | cyclohexyl | |

-continued

| No. | R¹ | R² | (R—Y—aromatic) | X | R | NMR (CDCl₃; ppm) |
|---|---|---|---|---|---|---|
| 63 | CH₃ | allyl | —CH=CH— | 4F | iso-propyl | |
| 64 | CH₃ | allyl | —CH₂—CH₂— | 4F | cyclohexyl | |
| 65 | CH₃ | allyl | —CH₂—CH₂— | 4F | iso-propyl | |
| 66 | C₂H₅ | CH₃ | —O—CH₂— | H | cyclohexyl | |
| 67 | n-C₄H₉ | CH₃ | —O—CH₂— | H | cyclohexyl | |
| 68 | n-C₄H₉ | —CH₂—O— | H | n-propyl | | |
| 69 | CH₃ | allyl | —CH₂—O— | H | n-propyl | |
| 70 | CH₃ | propargyl | —CH₂—O— | H | n-propyl | |
| 71 | CH₃ | CH₃ | —S—CH₂ | H | CH₃ | |
| 72 | CH₃ | CH₃ | —S—CH₂ | H | C₄H₉ | |
| 73 | CH₃ | CH₃ | —S—CH₂ | H | C₁₀H₂₁ | |
| 74 | CH₃ | CH₃ | —S—CH₂ | H | cyclohexyl | |
| 75 | CH₃ | CH₃ | —S—CH₂ | H | 1-methyl-2-propenyl- | |
| 76 | CH₃ | CH₃ | O | H | H | m.p. 129° C. |
| 77 | CH₃ | CH₃ | —CH₂—CH₂ | H | 1-ethylpentyl | s 7.6 1H; m 7.4–7.0 4H; s 3.90 3H; s 3.8 3H; m 2.4–2.3 2H; m 1.6–0.7 17H |
| 78 | CH₃ | CH₃ | —CH₂CH₂ | H | 2,6-dimethylheptyl | s 7.6 1H; m 7.3–7.0 4H; s 3.9 3H; m 2.5–2.35 2H; m 1.6–0.7 20H |
| 79 | CH₃ | CH₃ | —CH=CH— | H | 1-ethyl-pentyl | s 7.6 1H; m 7.65–7.1 4H; d 6.3 2H; m 5.95–5.8 1H; s 3.8 3H; s 3.7 3H; m 2.1–0.8 15H |
| 80 | CH₃ | CH₃ | —CH=CH— | H | 2,6-dimethylheptyl | s 7.6 1H; m 7.65–6.8 5H; m 6.25–6.15 1H; m 6.0–5.9 1H; m 5.2–5.0 1H; s 3.8 3H; s 3.7 3H; m 2.3–1.45 13H |
| 81 | CH₃ | CH₃ | —CH=CH— | H | n-heptyl | 2.7.6 1H; m 7.6–7.0 4H; m 6.4–6.0 2H; s 3.8 3H; s 3.7 3H; m 2.25–2.15 2H; m 1.6–0.8 13H |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Hemileia vastratrix in coffee,
Alternaria solani in potatoes and tomatoes,
Sclerotium rolfsii in groundnuts and lawns, and
Fusarium and Verticillium species in various plants.

The compounds are applied by spraying or dusting the plants with the active ingredients, or treating the seeds of the plants with the active ingredients. They may by applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all event ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene, benzene), chlorinated aromatics (e.g., chlorobenzenes), paraffins (e.g., crude oil fractions), alcohols (e.g., methanol, butanol), ketones (e.g., cyclohexanone), amines (eg., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt% of active ingredient.

The application rate are from 0.02 to 3 kg or more of active ingredient per hectare, depending on the type of effect desired. The novel compounds may also be used for protecting materials, inter alia for combating wood-destroying fungi such as Coniophora puteana and Polystictus versicolor. The novel active ingredients may also be used as fungicidal components of oily wood preservatives for protecting wood against wood-discoloring fungi. They are applied by treating, for example impregnating or painting, the wood with them.

The agents and the ready-to-use formulations prepared from them, such as solutions, emulsions, suspensions, powders, dusts, pastes and granules, are applied in conventional manner, for example by spraying, atomizing, dusting, scattering, dressing or watering. Examples of formulations are given below.

I. 90 parts by weight of compound no. 2 is mixed with 10 parts by weight of N-methyl-alpha-pyrrolidone. A mixture is obtained which is suitable for application in the form of very fine drops.

II. 20 parts by weight of compound no. 8 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of caster oil. By pouring the solution into water and uniformly distributing it therein, an aqueous dispersion is obtained.

III. 20 parts by weight of compound no. 17 is dissolved in a mixture consisting of 40 parts by weight of cyclohexane, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into water and finely distributing it therein, an aqueous disperion is obtained.

IV. 20 parts by weight of compound no. 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 8 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 17 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 2 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 3 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicial action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithioccarbamate and
N,N'-polypropylenebis(thiocarbamyl)disulfide;
nitro derivative, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2,3-dicyano-1,4-dithiaanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N',-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiin,
2,3-dihydro-5-carboxanilido-6-methyl-1,4-oxathiin 4,4-dioxide,
2-methyl-5,6-dihydro-5H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts, N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorphenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorohenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2thioureido)-benzene,
and various fungicides, such as
dodecylguanidine acetate,
3-[3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroaceetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoxyimino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol.

The prior art active ingredients used in the following experiments for comparison purposes were N-tridecyl-2,6-dimethylmorpholine (A), its acetate (B) and methyl α-(2-benzyloxyphenyl-β-methoxyacrylate (C).

USE EXAMPLE 1

Action on wheat mildew

Leaves of pot-grown wheat seedlings of the "Fruüh-gold" variety were sprayed with aqueous liquors containing (dry basis) 80% of active ingredient and 20% of emulsifier, and sprayed, 24 hours after the sprayed-on layer had dried, with spores of wheat mildew (*Erysiphe graminis* var. tritici). The plants were then set up in the greenhouse at 20° to 22° C. and a relative humidity of 75 to 80%. The extent of mildew spread was assessed after 7 days.

The results obtained show that active ingredients nos. 1, 2 and 3, applied as 0.025 and 0.006 wt% spray liquors, had a better fungicidal action (90%) than prior art active ingredients A and B (70%).

EXAMPLE 2

Action on brown rust of wheat

Leaves of pot-grown wheat seelings of the "Früh-gold" variety were dusted with spores of brown rust (*Puccinia recondita*). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results obtained show that compounds 1, 2 and 3, applied as 0.025% and 0.006 wt% spray liquors, had a better fungicidal action (100%) than comparative agents A and C (70%).

USE EXAMPLE 3

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 10 days in the greenhouse. Then the leaves were infected with a zoospore suspension of *Plasmopara viticola*. The plants were first placed for 16 hours in a water vapor-saturated chamber at 24° C. and then in a greenhouse for 8 days at from 20° to 30° C. To accelerate and intensify the sporangiophore discharge, the plants were then again placed in the moist chamber for 16 hours. The extend of fungus attack was then assessed on the undersides of the leaves.

The results obtained show that for example compounds 1, 2, 3 and 4, applied as 0.05% spray liquors, had a good fungicidal action (100%).

USE EXAMPLE 4

Action on *Septoria nodorum*

Leaves of pot-grown wheat seedlings of the "Jubilar" variety were sprayed with aqueous liquors containing (dry basis) 80% of active ingredient and 20% of emulsifier. After the sprayed-on layer had dried, the leaves were cut off and placed in dishes containing 25 ppm of an aqueous benzimidazole solution. The leaves were then infected with an aqueous spore suspension of *Septoria nodorum*, and the dishes covered. The extent of fungus spread was determined after the dishes had stood for 7 days at 20° to 22° C.

The results obtained show that for instance compounds 1, 2, 3 and 4, applied as 0.05% spray liquors, had a good fungicidal action (100%).

We claim:

1. A substituted acrylate of the formula:

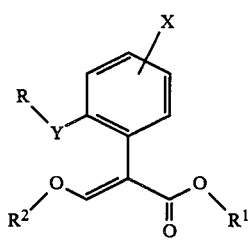

wherein $R^1$ and $R^2$ are identical or different and each represents $C_1-C_8$-alkyl, $C_2-C_8$-alkenyl or $C_3-C_8$-akynyl; X is hydrogen, halogen, $C_1-C_4$-alkyl, $C_1-C_4$-alkoxy, trifluoromethyl, cyano or nitro; Y is ethylene, ethenylene, methyleneoxy, oxymethylene, thiomethylene, methylenethio or oxygen; R is n-decyl, n-pentadecyl, n-octadecyl, n-eicosanyl, methoxyethyl, butoxyethyl, methoxycarbonylethyl, cyclopropyl, dichlorocyclopropyl, cyclooctyl, 2,6-dimethyl-2,6-octadiene-8-yl, $C_6-C_8$-cycloalkenyl, $C_3-C_{10}$-alkynyl and $C_8$-cycloalkynyl; and $R^3$ has the same definition as $R^1$ and is identical to or different from $R^1$.

2. Methyl α-(2-(2,6-dimethyl-2,6-octadienyloxy)-phenyl)-β-methoxyacrylate.

3. Methyl α-(2-(2,6-dimethyloctanoyloxy)-phenyl)-β-methoxyacrylate.

4. Methyl α-(2-(2,6,10-trimethyl-2,6,10-dodecyltrienyloxy)-phenyl)-β-methoxyacrylate.

5. Methyl α-(2-(2,6,10,14-tetramethyl-2,6,10,14-hexadecatetraenyloxy)phenyl)-β-methoxyacrylate.

6. A fungicide containing a carrier and a substituted acrylate of the formula:

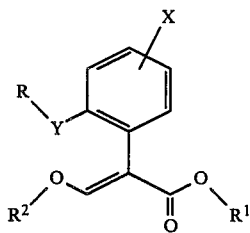

wherein $R^1$ and $R^2$ are identical or different and each represents $C_1-C_8$-alkyl, $C_2-C_8$-alkenyl or $C_3-C_8$-alkynyl; X is hydrogen, halogen, $C_1-C_4$-alkyl, $C_1-C_4$-alkoxy, trifluoromethyl, cyano or nitro; Y is ethylene, ethenylene, methyleneoxy, oxymethylene, thiomethylene, methylenethio or oxygen; R is n-decyl, n-pentadecyl, n-octadecyl, n-eicosanyl, methoxyethyl, butoxyethyl, methoxycarbonylethyl, cyclopropyl, dichlorocyclopropyl, cyclooctyl, 2,6-dimethyl-2,6-octadiene-8-yl, $C_6-C_8$-cycloalkenyl, $C_3-C_{10}$-alkynyl and $C_8$-cycloalkynyl; and $R^3$ has the same definition $R^1$ and is identical to or different from $R^1$.

7. A process for controlling fungi, wherein fungi or materials, plants, seeds or soil threatened by fungus attack are treated with a fungicidally effective amount of a substituted acrylate of the formula:

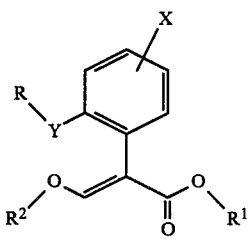

wherein $R^1$ and $R^2$ are identical or different and each represents $C_1-C_8$-alkyl, $C_2-C_1$-alkenyl or $C_3-C_8$-alkynyl; X is hydrogen, halogen, $C_1-C_4$-alkyl, $C_1-C_4$-alkoxy, trifluoromethyl, cyano or nitro; Y is ethylene, ethenylene, methyleneoxy, oxymethylene, thiomethylene, methylenethio or oxygen; R is n-decyl, n-pentadecyl, n-octadecyl, n-eicosanyl, methoxyethyl, butoxyethyl, methoxycarbonylethyl, cyclopropyl, dichlorocyclopropyl, cyclooctyl, 2,6-dimethyl-2,6-octadiene-8-yl, $C_6-C_8$-cycloalkenyl, $C_3-C_{10}$-alkynyl, and $C_8$-cycloalkynyl; and $R^3$ has the same definition as $R^1$ and is identical to or different from $R^1$.

* * * * *